(12) United States Patent
Karami et al.

(10) Patent No.: US 6,936,129 B2
(45) Date of Patent: Aug. 30, 2005

(54) METHOD OF MAKING A WINGED ABSORBENT ARTICLE

(75) Inventors: Hamzeh Karami, Lockhaven, PA (US); Donald Roy Dodelin, Woodstock, GA (US)

(73) Assignee: First Quality Products, Inc., State College, PA (US)

( * ) Notice: Subject to any disclaimer, the term of this patent is extended or adjusted under 35 U.S.C. 154(b) by 437 days.

(21) Appl. No.: 09/891,976

(22) Filed: Jun. 26, 2001

(65) Prior Publication Data

US 2001/0042584 A1 Nov. 22, 2001

Related U.S. Application Data

(63) Continuation-in-part of application No. 09/797,334, filed on Mar. 1, 2001, now abandoned, which is a continuation-in-part of application No. 09/097,198, filed on Jun. 12, 1998.

(51) Int. Cl.[7] .............................. B32B 31/00
(52) U.S. Cl. ..................... 156/265; 156/300; 156/301; 156/302; 156/303; 156/201; 156/204; 156/227; 156/512; 156/514; 156/518; 156/519; 156/520; 156/517
(58) Field of Search ................................ 156/517, 303, 156/265, 300, 301, 302, 201, 204, 227, 512, 514, 518, 519, 520, 513

(56) References Cited

U.S. PATENT DOCUMENTS 5,399,219 A * 3/1995 Roessler et al. ............ 156/259
5,683,533 A * 11/1997 Keighley et al. ........... 156/204
5,704,928 A 1/1998 Morita et al.
6,579,275 B1 * 6/2003 Pozniak et al. ............. 604/390

FOREIGN PATENT DOCUMENTS

| EP | 0 972 501 A2 | 1/2000 |
| EP | 0 985 398 A1 | 3/2000 |
| EP | 1 004 285 A1 | 5/2000 |

* cited by examiner

*Primary Examiner*—Linda L Gray
(74) *Attorney, Agent, or Firm*—Amster Rothstein & Ebenstein, LLP

(57) ABSTRACT

A method is provided for continuous mass production of winged absorbent articles, including T-shaped absorbent articles, by attachment of wing portions to the chassis of the absorbent article which comprises a topsheet, a backsheet and a core sandwiched between the topsheet and the backsheet. The method comprises feeding at least one web of wing-making material, which may be at least partly elasticated, simultaneously attaching landing zones in spaced apart relationship on a surface of the web, attaching tape tabs on the edge of the web, folding the web longitudinally in a generally Z-fold configuration, feeding the chassis of the absorbent article in the general direction of the web, severing individual folded wing portions from said web and attaching the winged portions to the chassis at predetermined spaced intervals.

33 Claims, 3 Drawing Sheets

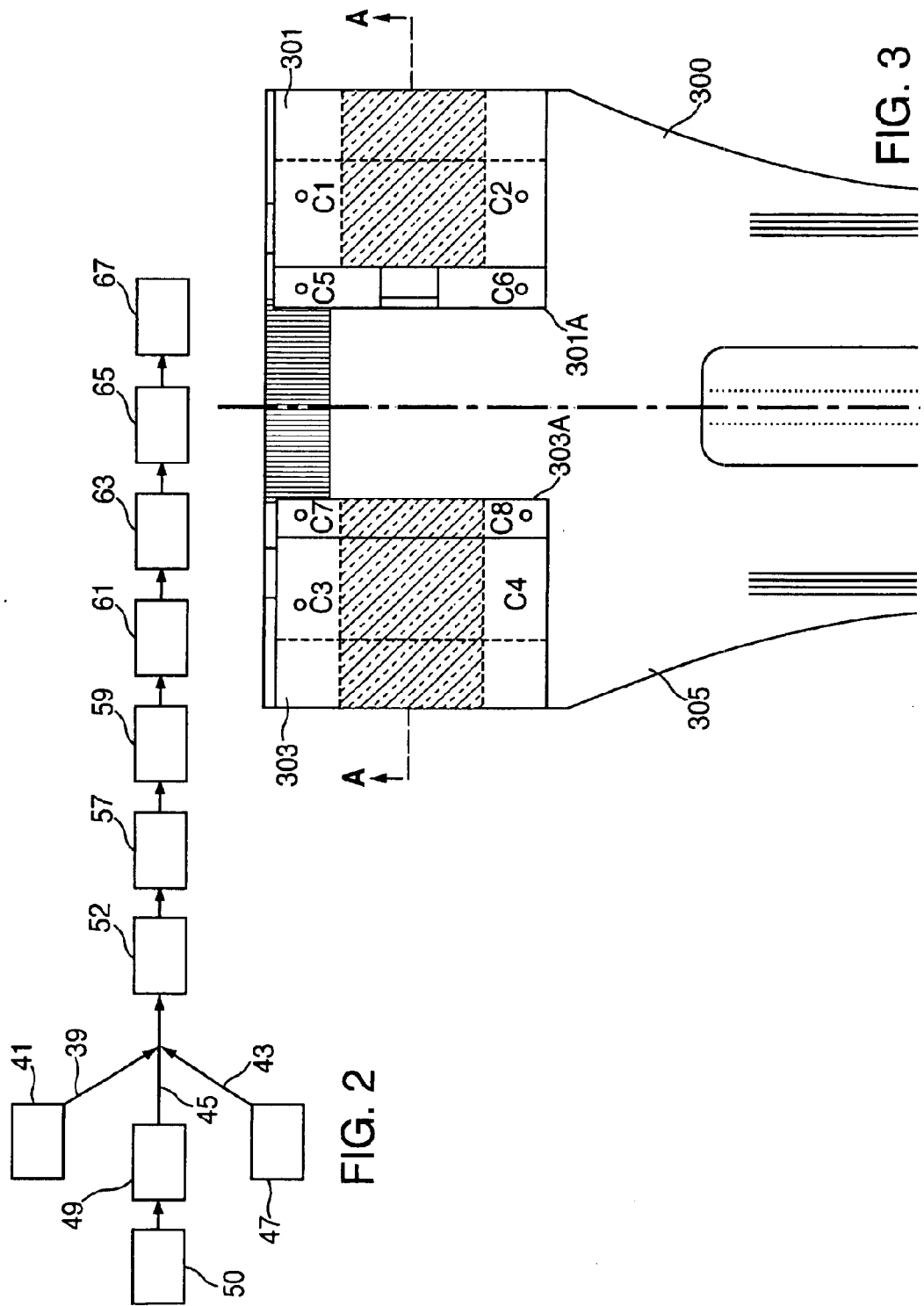

METHOD OF MAKING A WINGED ABSORBENT ARTICLE

RELATED APPLICATIONS

This application is a continuation-in-part of application Ser. No. 09/797,334, filed Mar. 1, 2001 now abandoned.

FIELD OF THE INVENTION

The present invention relates generally to a method of making absorbent articles with wings (flaps) and is particularly related to a method of attaching wings to the chassis of an absorbent article. In one specific aspect, the present invention relates to a method of attaching wings to the chassis of an absorbent article by a continuous method which is suitable for commercial production. In another specific aspect, the present invention relates to such method for formation of T-shaped absorbent articles.

BACKGROUND OF THE INVENTION

Absorbent articles such as diapers, incontinent undergarments, sanitary napkins and the like are widely used in various homes, hospitals and health care institutions. Typically, an absorbent article such as, e.g., a diaper, comprises a chassis defined basically by a liquid permeable topsheet, a liquid impervious backsheet and an absorbent sheet or layer sandwiched between the topsheet and the backsheet. Sometimes, the chassis may also include an acquisition layer disposed between the topsheet and absorbent sheet and one or more other layers for one purpose or another. The chassis itself has a front waist section and a backwaist section, the waist section being somewhat flared so that the flared portion may be wrapped around the torso of the wearer, and fastening means or adhesive strips are used to secure the flared portions (wings) together.

In order to improve securement of the diaper around the waist of the wearer, so-called T-shaped diapers have been proposed and described in several prior art patents. One T-shaped absorbent article has been described in U.S. Pat. No. 4,995,873 issued to Jackilyn M. Knight on Feb. 26, 1991. The absorbent article described by Knight has a crosspiece and an intersecting piece, which together form a generally T-shaped configuration when the article is laid out flat. Releasable fastening means such as press-on/rip-off adhesive or Velcro® strips are used to attach the crosspiece and intersecting piece together.

Commonly assigned, copending application Ser. No. 09/797,334, filed Mar. 1, 2001, describes a T-shaped absorbent article, e.g., a diaper with emphasis on the type of fastening system used in order to enhance securement of diaper to the body. The prior art patents discussed in said copending application describe other T-shaped absorbent garments. One patent mentioned therein, U.S. Pat. No. 5,906,604 issued on May 25, 1999 to Ronnberg et al., describes an attachment means for a belt used with an absorbent garment. The belt is either integrated with the absorbent garment, or it can be separately attached thereto by means of a releasable attachment system such as hook and loop type fastening means, e.g., Velcro®.

Regardless of whether the absorbent article is T-shaped or the more traditional type, it is generally recognized that their commercial production involves the use of complicated machinery and equipment. The paramount consideration in the design and operation of such machinery and equipment is the efficiency of production and quality of the absorbent garments which are produced. The efficiency of production depends, in turn, on the effectiveness of the method of assembly of the component parts of the absorbent garment. These are serious considerations in the economic and competitive fabrication of absorbent garments, particularly the recently used T-shaped absorbent garments.

Therefore, it is an object of the present invention to provide an efficient and commercially viable method of manufacturing absorbent articles.

It is also an object of the present invention to provide a method of manufacturing absorbent articles having wings or flaps attached to the chassis of the article.

It is a further object of the present invention to provide a continuous method of attaching wings to the chassis of an absorbent article such as a T-shaped brief.

It is yet another object of the present invention to provide a continuous method of forming a T-shaped diaper complete with all basic components of the diaper, including a fastening system, ready for shipment from the manufacturing plant.

The foregoing and other features and objects of the present invention will become more apparent from the ensuing description and the accompanying drawings.

SUMMARY OF THE INVENTION

In accordance with this invention, winged absorbent articles are produced by a method which is continuous, efficient and capable of mass production. The method basically comprises attaching wings to the chassis of an absorbent article, said chassis comprising a topsheet, a backsheet and an absorbent layer (core) sandwiched between the topsheet and the backsheet. The method comprises feeding at least one web of wing-making material, in a general machine direction, attaching a plurality of landing zones in spaced apart relationship on a surface of the web, said landing zone being perforated, or non-perforated if desired, followed by attaching tape tabs on the edge of said web. As the web advances in the machine direction, it is longitudinally Z-folded and a temporary bond is formed on the Z-folded portion. Simultaneously with folding said web, the chassis of the absorbent article is fed in the machine direction, and individual folded wing portions are severed and attached to the chassis of the absorbent article at predetermined spaced intervals. The method also contemplates feeding the web and the chassis in cross directions, however, means is provided for causing the web and/or the chassis to travel in the same direction at the point of attachment of the wings to the chassis.

BRIEF DESCRIPTION OF THE DRAWINGS

In the drawings, wherein like reference numerals are employed to designate like parts wherever possible:

FIG. 2 is partly schematic, partly block diagram showing the formation of the chassis of the absorbent article and the subsequent steps of preparing the absorbent article for shipment and storage;

FIG. 3 is a partial cutaway of a T-shaped absorbent article, viewed when laid out flat, with each wing folded upon itself toward the vertical axis of the garment;

DETAILED DESCRIPTION OF THE INVENTION

Figure 1:
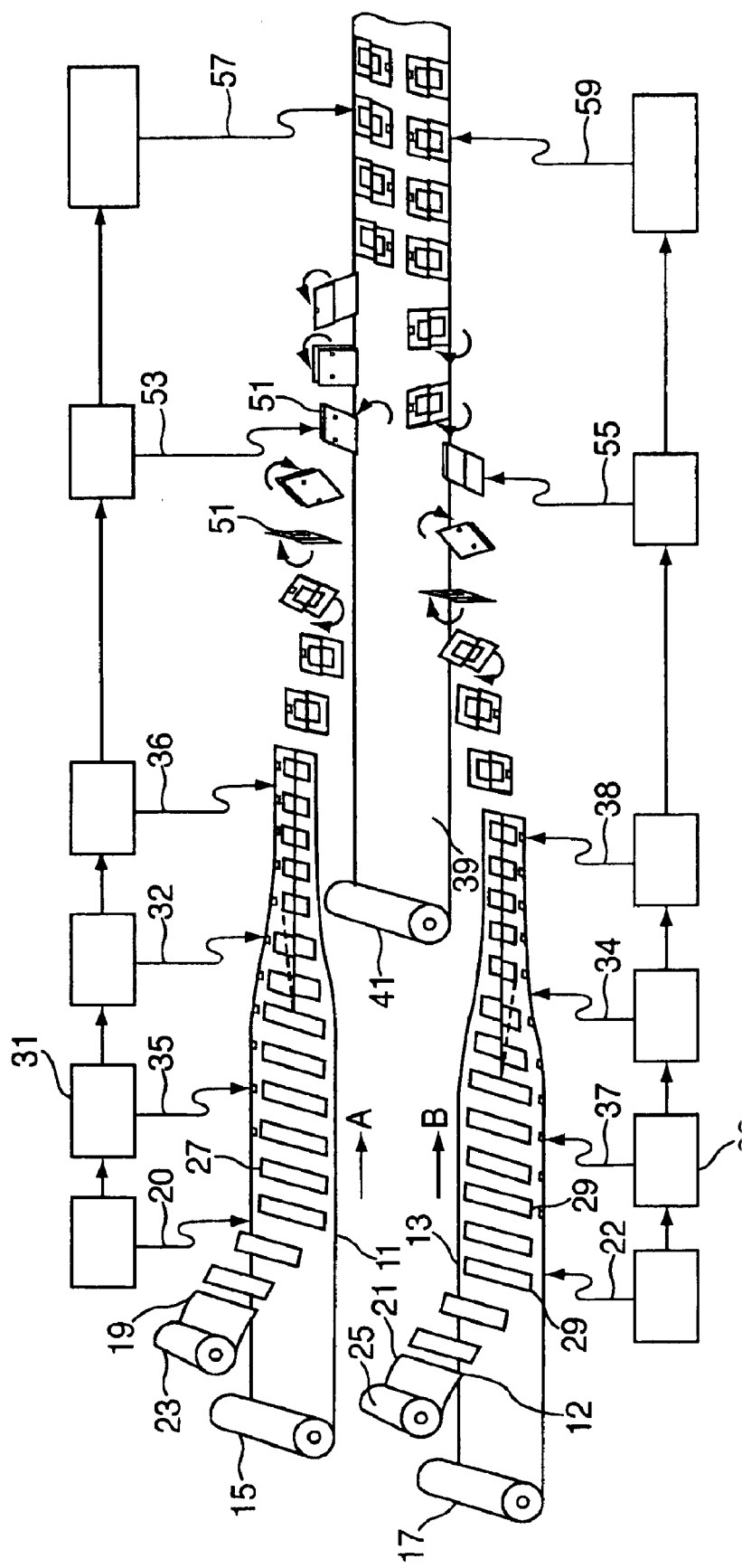
FIG. 1 is a schematic flow diagram illustrating the method of this invention.

Referring to FIG. 1, two webs of wing material 11 and 13 are unwound from the respective feed rollers 15 and 17 with the webs moving in a generally parallel, spaced apart relation in the direction of the arrows A and B, in the machine direction, at the same predetermined speed. As the webs 11 and 13 advance in the machine direction, webs 19 and 21 of landing zone material are unwound from the respective feed rollers 23 and 25, moving in the same direction as the webs 11 and 13, a predetermined speed. As the webs 19 and 21 advance, individual strips of landing zones 27 and 29 are cut by a cutting means such as rotating blade (not shown) and each strip of landing zone 27 and 29, which may be precoated with pressure sensitive adhesive, is attached on the surface of each web 11 and 13 at stations 20,22. If the landing zone is not precoated with adhesive, the adhesive should be coated on the bottom surface of the landing zone prior to cutting the landing zone to individual pieces. The individual landing zone strips are attached to the wing surface of each web 11 and 13 in spaced apart relationship, as the webs move in the machine direction, and are usually precut to the desired dimensions. The landing zones 27 and 29 may be perforated in which case the webs 19 and 21 must be perforated before winding them on their respective feed rollers 23,25. Obviously, if no landing zone is needed or desired, this step, i.e., attachment of landing zone strips to the surface of the webs 11 and 13 is omitted, in which case the feed rollers 23 and 25 are not used. The method of this invention also contemplates perforating the landing zone in line, in which case a perforation station is employed in the process line. Thus each of the webs 19 and 21 must be perforated individually or the landing zone may be perforated after attaching the landing zones on the wings. The exact manner and details of perforation of the landing zone are generally well known to those skilled in the art. Also, the webs 11, 13 may be at least partly elasticated in the cross machine direction, if desired.

Continuing with the method of this invention by reference to FIG. 1, after the landing zone strips 27 and 29 have been attached on the surface of the webs 11 and 13, a wing tape is attached to the outer edge of either or both webs 11 and 13. As shown in FIG. 1, tape dispensing stations (rollers) 31 and 33 on each side of the webs 11 and 13 dispense the tapes as shown at 35 and 37, which are secured to the edge of the respective webs. The timing of attachment of the tapes to each web is synchronized with the speed of movement of the webs and the attachment of the landing zone strips to the webs. After attachment of the wing tapes each of the moving webs 11 and 13 is longitudinally folded by a folding means (not shown in drawing) at the folding stations 32,34, to form a generally Z-fold, followed by temporarily (releasably) bonding the Z-folded wing layers to itself at the stations 36,38, in order to form a folded web which is narrower than the width of the webs 11,13 prior to folding. Temporary bonding of the folded wing is achieved by the application of a releasable adhesive which serves to prevent the wing from unfolding as it passes through the diaper-making machine. Longitudinal folding of each web facilitates stacking, packaging and storage of the final product (diaper) prior to shipment for use.

As is further shown in FIG. 1, the method of this invention also comprises simultaneous feeding of the top sheet 39 from the topsheet feed roller 41 in the machine direction. Simultaneously, a backsheet layer 43 and an absorbent layer 45 are fed from the respective backsheet feed roller 47 and the absorbent layer feed roller 49 to combine with the topsheet thereby forming the chassis of the diaper with the absorbent layer or pad sandwiched between the topsheet and the backsheet. A pulp fluffing station 50 feeds pulp to the absorbent layer station 49 for mixing with the absorbent layer 45. At about the point of combining the topsheet, the backsheet and the absorbent layer at station 52, the individual Z-folded wings 51 are cut and permanently bonded to the topsheet 39 at stations 53,55. Permanent bonding of the individual wings 51 to the topsheet 39 is effected by a suitable permanent adhesive intended to keep the wing attached to the chassis of the absorbent article during its use. As the chassis further advances in the machine direction with the wings attached thereto, the wings are again folded over the top surface of the coversheet as in 55,57 and a temporary bond such as, e.g., a releasable adhesive, is applied thereto to form a second temporary (releasable) bond, thus bonding the perforated wing on the coversheet.

The order of bonding is not per se critical. Thus, the wing can be first permanently bonded to the chassis (e.g., to the topsheet), then folded onto the top surface of the diaper (topsheet) to be bonded temporarily, instead of attaching each wing to the coversheet as described in connection with FIGS. 1 and 2 and folding as previously described, the prefolded wing can be attached to the backsheet and folded under the bottom surface of the backsheet and temporarily bonded as previously described.

Referring to FIG. 2, after the formation of the diaper chassis by combining the topsheet 39 from feed roller 41, the backsheet 43 from backsheet feed roller 47 and the absorbent layer 45 from feed roll between said layers, shown in block at 52, the diaper chassis is cut at 61, the cut chassis is finally folded at 63, stacked at stacking station 65, packaged at 67 and stored at storage station 69.

A stretched view of a diaper, partly broken away, with folded wings, is shown in FIG. 3. As shown in this figure, each of the wings 301,303 is folded upon itself toward the center of the chassis 300. The facing surfaces of each wing 301,303 may be attached to each other by a removable (releasable) adhesive, by ultrasonic means, or some other suitable attachment means, as indicated by the dotted circles C1, C2, C3 and C4. Each of the folded wings 301 and 303 is folded over the top surface of the coversheet as shown by the dotted circles C5, C6, C7 and C8. In order to use the diaper, each of the wings 301,303 has a finger lift portion 301A,303A which may be gripped between the thumb and the forefinger and lifted to an open position.

Figure 4:
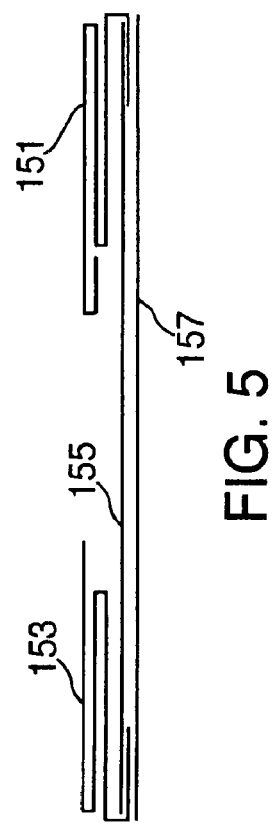
FIG. 4 is a sectional view taken along the line 4—4 in FIG. 3.

Referring to FIG. 4, the wings 41, 43 are shown folded over the topsheet 45 in accordance with one folding embodiment. Also shown in this figure is backsheet 47 and tape tab 49 attached to an edge of the topsheet.

Figure 5:
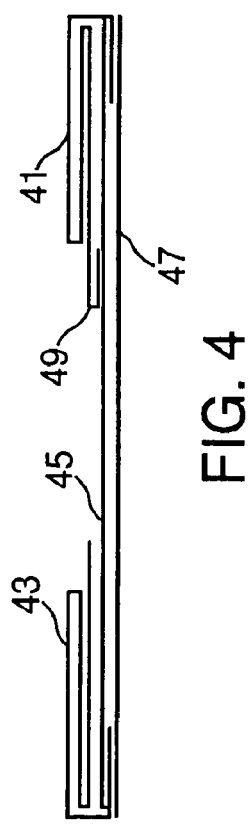
FIG. 5 is a sectional view similar to FIG. 4 illustrating a different way of folding the wings.
Figure 6:
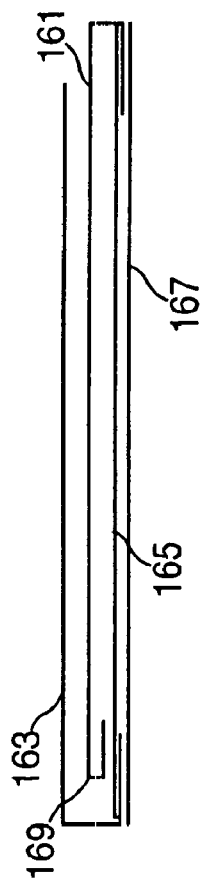
FIG. 6 is another sectional view similar to FIG. 4 illustrating still another way of folding the wings.

FIGS. 5 and 6 illustrate further folding techniques. In FIG. 5, the wings 151,153 are folded with tape tab 159 attached to the wing 151. In this case the fold layer having the tape tab is the uppermost layer as compared to the layer with tape is the lowermost layer. The wings 151,153 are disposed above the topsheet 155 and backsheet 157. FIG. 6 illustrates a fold wherein the wing 161 is disposed under the fold 163 with the tape tab 169 attached to the wing 161. In this case each wing is folded over the top surface of the coversheet 165 disposed above the backsheet 167.

The materials and fabrics used in making the diapers of the present invention are generally of the type and variety known in the art and are described, for example, in U.S. Pat.

Nos. 4,695,278 and 4,795,454 and in copending, commonly assigned application Ser. No. 09/149,265, filed Sep. 8, 1998, the disclosures of which are fully incorporated herein by reference. Thus, the liquid previous cover sheet is a compliant soft material which is skin friendly and does not cause rash or irritation. Such materials include porous foams, reticulated foams, plastics, natural fibers such as woods or cotton fibers, synthetic fibers made of polyester, polypropylene or from a combination of such materials. The topsheet may also be preferably made of spunbond nonwoven polypropylene, i.e., available from First Quality Nonwoven, Inc., Hazelton, Pa., and is usually coextensive with the backing film. In general, however, the various layers are of the type and materials well known in the diaper industry and are within the scope and knowledge of those versed in this art.

The absorbent pad or core may be manufactured from a wide variety of liquid absorbent materials of the type usually used in manufacturing disposable diapers and other absorbent articles. Such materials include comminuted wood pulp, creped cellulose wadding, absorbent foams and sponges, super absorbent polymers, or a combination of said materials.

The backsheet or film backing is usually a polyethylene layer which is liquid, air and preferably vapor impermeable, and is placed under the absorbent core to prevent the body exudates from leaking and otherwise soiling the user's bed and clothing. The width and length of the backing film (or composite film nonwoven laminate) are generally wider and longer than the width and length of the absorbent core. Polyethylenes suitable as backing film for the purpose of this invention are available from Cloplay Plastics, Cincinnati, Ohio.

An acquisition layer may also be used in some instances. If so, the acquisition layer is usually made of chemically bonded nonwoven polyester available from American Nonwovens, Columbus, Mo. Preferably, the width of this layer is substantially the same as the width of the crotch absorbent core. This core may be made of wood pulp fibers and super absorbent polymers (SAP) such as IM 7000 series available from Clarian Products, Inc., Portsmouth, Va., and Chemdal 2000 series available from Chemdal, Inc., Palantine, Ill. Alternatively, the absorbent core may be made of dual layer construction, in which case, the absorbent polymer may be securely position between each layer of the absorbent material.

Other layers may be used in making the chassis depending on the ultimate use of the absorbent garment. It must be noted, however, that the present invention is directed to the method of manufacturing the absorbent article regardless of the type and kind of the different layers used in forming such articles.

Also, while the fastening system in the method of this invention has been described with reference to landing zone strips and tape tabs, the landing zone may be a loop material and a complimentary male element may be used as the tape, as described in the aforementioned copending application Ser. No. 09/797,334 filed Mar. 1, 2001. The use of such fastening systems are within the purview of the method described herein.

What is claimed is:

1. A method of making a winged absorbent article having a chassis comprising a topsheet, a backsheet and an absorbent core sandwiched between said topsheet and said backsheet, wherein said method comprises:
    (a) feeding at least one web of wing-making material, said web having an upper surface and an opposed lower surface,
    (b) attaching a plurality of landing zones in spaced apart relationship, on one surface of said web,
    (c) attaching at least one wing tab on the edge of said web,
    (d) longitudinally folding said web in a generally Z-fold configuration and forming a releasable bond on said longitudinal fold,
    (e) feeding said chassis in one direction, and
    (f) severing individual folded wing portions from said web and attaching each of said individual folded wing portions to said chassis at predetermined spaced intervals, while causing said web and said chassis to travel in the same direction at said point of attachment.

2. A method as in claim 1 wherein each of said wings is attached to said topsheet.

3. A method as in claim 1 wherein each of said wings is attached to said backsheet.

4. A method as in claim 1 wherein each of said wings is attached intermediate said topsheet and said backsheet.

5. A method as in claim 1 wherein said landing zones are perforated.

6. A method as in claim 2 wherein said landing zones are perforated.

7. A method as in claim 3 wherein said landing zones are perforated.

8. A method as in claim 4 wherein said landing zones are perforated.

9. The method of claim 1 wherein said wings are at least partly elasticated.

10. The method of claim 2 wherein said wings are at least partly elasticated.

11. The method of claim 3 wherein said wings are at least partly elasticated.

12. The method of claim 4 wherein said wings are at least partly elasticated.

13. The method of claim 5 wherein said wings are at least partly elasticated.

14. The method of claim 6 wherein said wings are at least partly elasticated.

15. The method of claim 7 wherein said wings are at least partly elasticated.

16. The method of claim 8 wherein said wings are at least partly elasticated.

17. A method as in claims 1, 2, 3, 4, 5, 6, 7, 8, 9, 10, 11, 12, 13, 14, 15 or 16 wherein each of said folded wings is folded over the top surface of said topsheet and is releasably bonded to said topsheet.

18. A method as in claims 1, 2, 3, 4, 5, 6, 7, 9, 9, 10, 11, 12, 13, 14, 15 or 16 wherein each of said folded wings is folded under the bottom surface of said backsheet and is releasably bonded to said backsheet.

19. A method of making a winged absorbent article having a chassis comprising a topsheet, a backsheet and an absorbent core sandwiched between said topsheet and said backsheet, wherein said method comprises:
    (a) feeding at least one web of wing-making material, said web having an upper surface and an opposed lower surface,
    (b) attaching at least one wing tab on the edge of said web,
    (c) longitudinally folding said web in a generally z-fold configuration and forming a temporary bond on said longitudinal fold,
    (d) feeding said chassis in one direction, and
    (e) severing individual folded wing portions from said web and attaching each of said individual folded wing portions to said chassis at predetermined spaced intervals, while causing said web and said chassis to travel in the same direction at said point of attachment.

20. A method as in claim 19 wherein each of said wings is attached to said topsheet.

21. A method as in claim 19 wherein each of said wings is attached to said backsheet.

22. A method as in claim 19 wherein each of said wings is attached intermediate said topsheet and said backsheet.

23. A method as in claim 19 wherein said wings are at least partly elasticated.

24. A method as in claim 20 wherein said wings are at least partly elasticated.

25. A method as in claim 21 wherein said wings are at least partly elasticated.

26. A method as in claim 22 wherein said wings are at least partly elasticated.

27. The method of claims 19, 20, 21, 22, 23, 24, 25 or 26 wherein each of said folded wings is folded over the top surface of said topsheet and is releasably bonded to said topsheet.

28. The method of claims 19, 20, 21, 22, 23, 24, 25 or 26 wherein each of said folded wings is folded under the bottom surface of said backsheet and is releasably bonded to said backsheet.

29. A method as in claim 5 wherein each landing zone is perforated after attaching the landing zone to the web.

30. A method as in claim 6 wherein each landing zone is perforated after attaching the landing zone to the web.

31. A method as in claim 7 wherein each landing zone is perforated after attaching the landing zone to the web.

32. A method as in claim 8 wherein each landing zone is perforated after attaching the landing zone to the web.

33. A method as in claims 29, 30, 31 or 32 wherein each landing zone has a top surface and a bottom surface and wherein said bottom surface is coated with adhesive.

* * * * *